(12) United States Patent
Lindner

(10) Patent No.: US 7,009,697 B2
(45) Date of Patent: Mar. 7, 2006

(54) METHOD OF MONITORING CLOSURES ON CONTAINERS

(75) Inventor: Peter Lindner, Sunching (DE)

(73) Assignee: Krones AG, Neutraubling, DE (US)

( * ) Notice: Subject to any disclaimer, the term of this patent is extended or adjusted under 35 U.S.C. 154(b) by 255 days.

(21) Appl. No.: 10/381,834

(22) PCT Filed: Sep. 20, 2002

(86) PCT No.: PCT/EP02/10621

§ 371 (c)(1),
(2), (4) Date: Aug. 28, 2003

(87) PCT Pub. No.: WO03/024859

PCT Pub. Date: Mar. 27, 2003

(65) Prior Publication Data

US 2004/0042004 A1    Mar. 4, 2004

(30) Foreign Application Priority Data

Sep. 20, 2001 (DE) ................................ 101 46 449

(51) Int. Cl.
*G01N 21/00* (2006.01)
(52) U.S. Cl. ................................ 356/240.1; 250/223 B
(58) Field of Classification Search ............. 356/240.1, 356/239.4–239.6; 250/223 B
See application file for complete search history.

(56) References Cited

U.S. PATENT DOCUMENTS

| | | | | |
|---|---|---|---|---|
| 4,924,107 A | * | 5/1990 | Tucker | 250/559.46 |
| 5,301,238 A | * | 4/1994 | Apter et al. | 382/142 |
| 5,585,917 A | * | 12/1996 | Woite et al. | 356/237.1 |
| 5,699,152 A | * | 12/1997 | Fedor et al. | 356/240.1 |
| 6,237,418 B1 | | 5/2001 | Coughlin et al. | |
| 2004/0150815 A1 | * | 8/2004 | Sones et al. | 356/239.4 |

FOREIGN PATENT DOCUMENTS

| | | | |
|---|---|---|---|
| DE | 19540545 | | 5/1997 |
| GB | 926195 | | 5/1963 |
| JP | 405180621 A | * | 7/1993 |
| NL | 75871 | | 4/1954 |
| WO | WO 97/04887 | | 2/1997 |

* cited by examiner

*Primary Examiner*—Hoa Q. Pham
(74) *Attorney, Agent, or Firm*—Marshall, Gerstein & Borun LLP

(57) ABSTRACT

Method of optical inspection of closures on containers in which the outer edge of a closure is illuminated obliquely from above over the full circumference, and a photograph of the top side of the closure is made perpendicularly from above, and this photograph is used to detect the outer edge of the mouth, which appears brighter, and to check on the position of the cover logo relative to this edge of the mouth either directly or indirectly, and a signal is generated in the event an unacceptable eccentricity is found.

3 Claims, 2 Drawing Sheets

METHOD OF MONITORING CLOSURES ON CONTAINERS

FIELD OF THE INVENTION

This invention relates to a method of optical monitoring of closures on containers, in particular bottles or similar containers.

BACKGROUND OF THE INVENTION

The invention concerns detection of skewed or eccentric closures for the orifices of the containers in cases where these closures having a central logo on the top. Known devices for monitoring closures in bottle filling lines in the beverage industry are usually located in the area downstream from a filling and capping machine or they may be integrated into a complete bottle inspector. In the past, multiple views of the closure area of the mouth have been necessary for this function in order to be able to guarantee reliable detection of skewed closures.

SUMMARY OF THE INVENTION

The object of this invention is to reduce the complexity required to accomplish this.

This object is achieved by illuminating at least the outer edge of a closure over the full circumference by directing the light obliquely from above, and by taking a photograph of the top side of the closure perpendicularly from above and using this photograph to detect the outer edge of the mouth, which appears lighter, and inspecting the position of the cover logo relative to this edge of the mouth, and generating a signal in the event an unacceptable eccentricity is detected.

BRIEF DESCRIPTION OF THE DRAWINGS

One exemplary embodiment is explained below on the basis of the figures, which show.

DETAILED DESCRIPTION OF THE INVENTION

Figure 1:
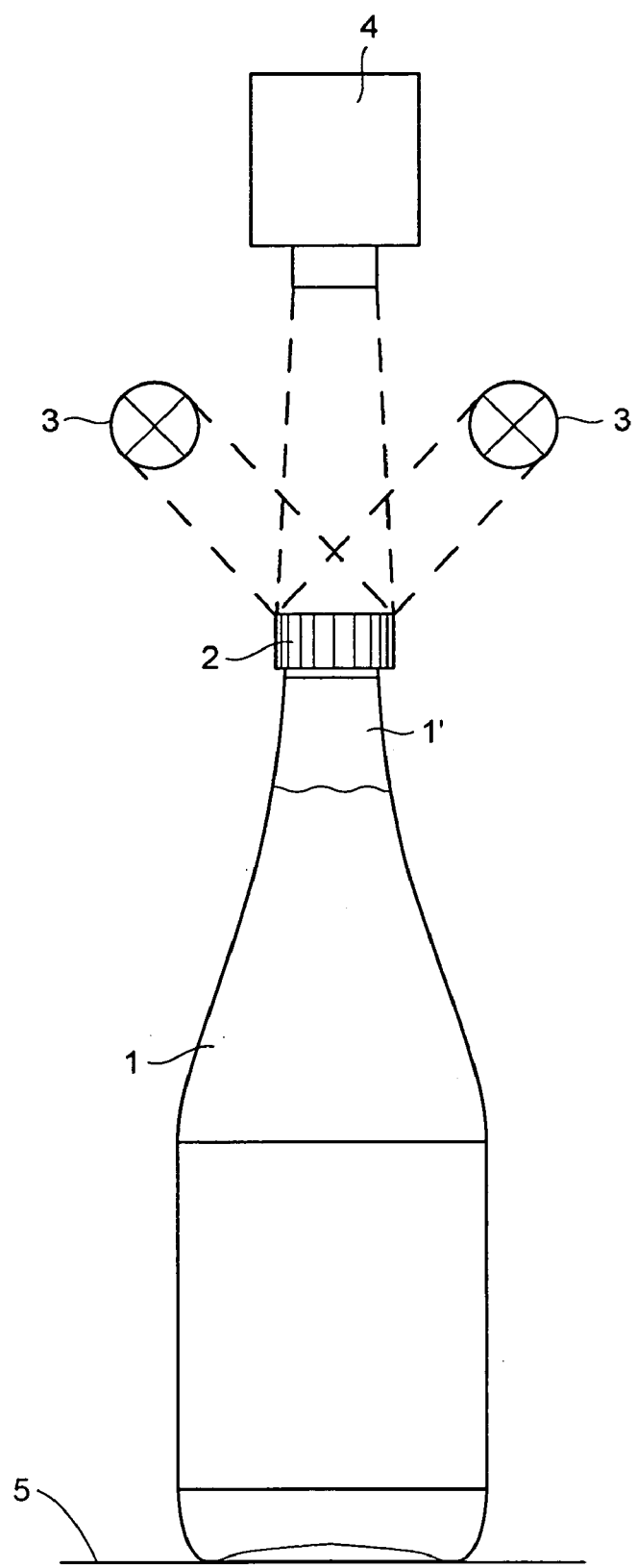
FIG. 1: a side view of an inspection device.

A CCD camera 4 having an image memory and a device (electronic image analyzer) for analyzing images recorded is mounted above a continuously drivable conveyor belt 5 and is aimed downward perpendicularly toward the conveyor belt; it is also used for generating a signal for displaying the results and/or rejecting bottles that do not conform to a specifiable standard.

A ring-shaped light source 3, which may consist of a plurality of LEDs, for example, positioned on a conical surface (inside surface) which is open toward the bottom and expands toward the outside, is arranged to be concentric with the optical axis of the camera. Pulsed LEDs are expediently synchronized with the camera and the movement of the bottles.

The height and geometry of the light source 3 are selected so that the closure 2 on the mouth of a bottle 1, which is beneath the camera 4 at the moment, its vertical central axis 1' being coaxial with the optical axis, can be illuminated over the full circumference obliquely from above and from the outside, in particular its outer edge, so that light striking the edge is reflected upward toward the camera 4.

As soon as the continuously moving bottle 1 has reached the coaxial position beneath the camera 4 as shown here, it photographs the closure 2, while the closure is being illuminated by the light source 3 at the same time, i.e., a photograph is made of the top side of the closure and is stored in the image memory of the electronic image analyzer of the camera. These processes are resolved in a known manner by an electronic control unit in combination with a photoelectric barrier trigger (not shown here), which detects the bottles as they pass by it.

Figure 2:
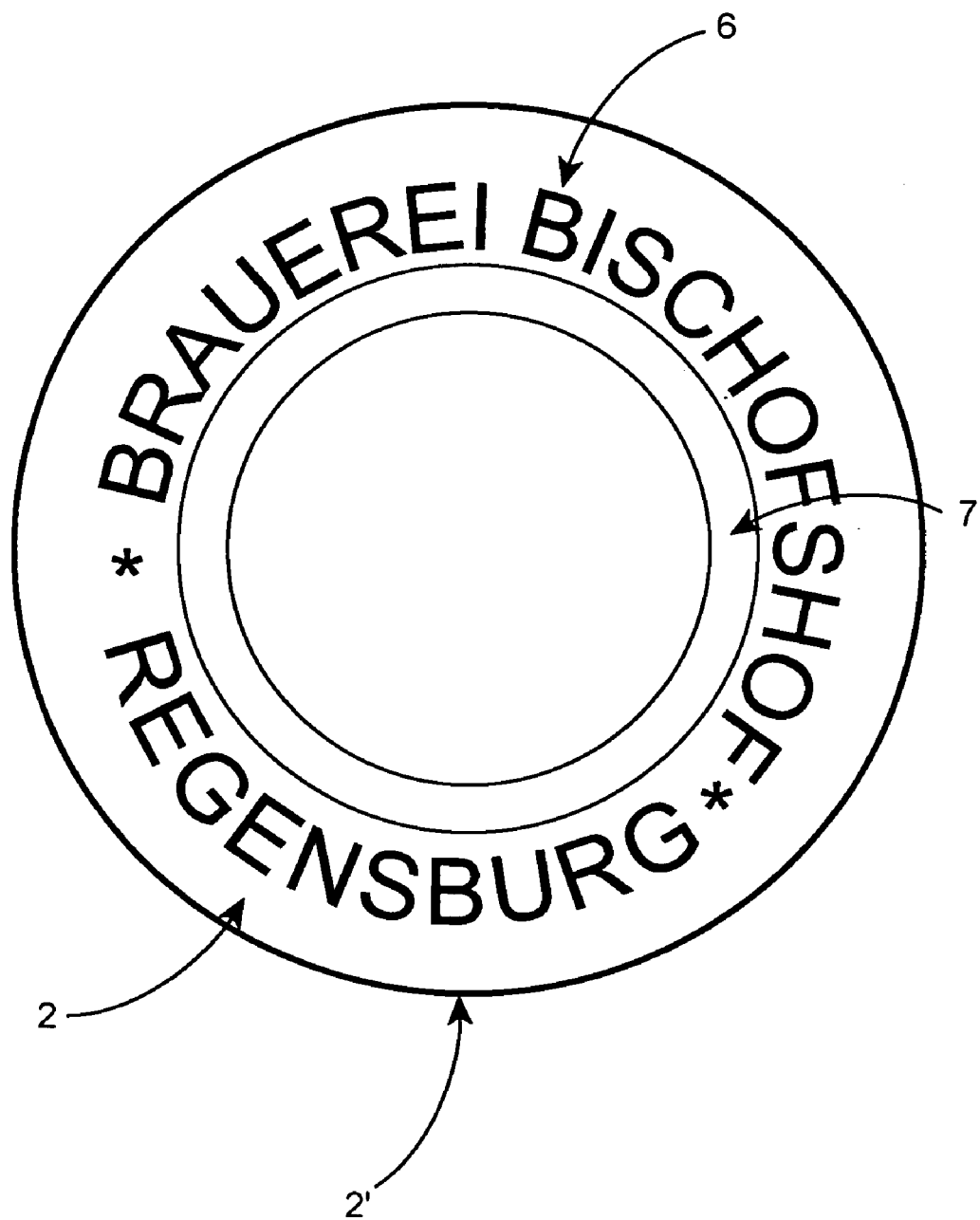
FIG. 2: an image of a mouth closure on a closed beverage bottle, this image having been recorded by the inspection device according to FIG. 1.

FIG. 2 shows a typical photograph of a crown cork closure for a glass bottle. As this shows, the cover logo on this closure has lettering 6 in a ring pattern, which should be concentric with the outer edge 2' of the closure, where the outer edge appears light due to the reflection of light, when the closure 2 is in its proper position. In the present case, however, the closure is positioned eccentrically.

To detect such a deviation, which might possibly occur, a centering analysis is performed by the electronic image analyzer on this lighted edge 2' with a high precision. Then a ring-shaped analysis gate 7, which exactly matches the respective cover logo, is generated to be precisely concentric with this edge 2', the outside circumference of this analysis gate 7 being adapted accordingly to the inside circumference of the lettering 6. In this way, it is possible to detect even minor deviations reliably, e.g., by measuring the distance between the outside circumference of the analysis gate 7 and the inside circumference of the lettering 6, and then, if necessary, a reject signal may be generated if the resulting value is outside the specified range of a predetermined limit value at a certain peripheral location or at any peripheral location.

In FIG. 2 the outside edge of the analysis gate 7 (in the 4 o'clock position) is at a distance from the inside edge of the lettering 6, while the diametrically opposite region (10 o'clock position) of the analysis gate 7 is already touching the inside edge.

This method can be used with all types of container closures such as screw-on closures, crown cork closures and pull-apart closures, as long as they have a cover logo having a decorative feature which is applied concentrically to the mouth of the container and can be used for this type of analysis.

I claim:

1. A method of optical inspection of closures on containers, comprising: illuminating the outer edge of a closure obliquely from above, making a photograph of the top side of the closure perpendicularly from above, using this photograph to determine the outer edge of the closure, which appears brighter, checking, either directly or indirectly, on the position of a cover logo relative to this edge, and generating a signal in the event an unacceptable eccentricity is found.

2. The method according to claim 1, and creating an analysis gate, which is concentric with the edge of the closure, for analyzing the photograph, the shape of this gate being adapted to the respective cover logo or parts thereof.

3. The method according to claim 2, and making one of a spot distance measurements, a distance measurement, and a combination thereof over all or part of the circumference.

* * * * *

UNITED STATES PATENT AND TRADEMARK OFFICE
CERTIFICATE OF CORRECTION

| | |
|---|---|
| PATENT NO. | : 7,009,697 B2 |
| APPLICATION NO. | : 10/381834 |
| DATED | : March 7, 2006 |
| INVENTOR(S) | : Peter Lindner |

It is certified that error appears in the above-identified patent and that said Letters Patent is hereby corrected as shown below:

On the Title Page:

At line Item (30), "101 46 449" should be -- 10146499 --,

At line Item (73), "Neutraubling, DE (US)" should be -- Neutraubling (DE) --.

In the Claims:

At Column 2, line 62, "measurements" should be -- measurement --.

Signed and Sealed this

Ninth Day of January, 2007

JON W. DUDAS
*Director of the United States Patent and Trademark Office*